United States Patent [19]

Shimomura et al.

[11] 4,073,933

[45] Feb. 14, 1978

[54] NOVEL BICYCLOHEPTENE DERIVATIVES

[75] Inventors: Hiromi Shimomura, Nishinomiya; Akihiko Sugie, Takarazuka; Junki Katsube, Toyonaka; Hisao Yamamoto, Kobe, all of Japan

[73] Assignee: Sumitomo Chemical Company, Limited, Osaka, Japan

[21] Appl. No.: 697,152

[22] Filed: June 17, 1976

[30] Foreign Application Priority Data

| | | |
|---|---|---|
| June 27, 1975 | Japan | 50-80292 |
| July 1, 1975 | Japan | 50-81635 |
| July 1, 1975 | Japan | 50-81636 |

[51] Int. Cl.[2] .................... C07C 177/00; C07C 61/38; C07C 69/74

[52] U.S. Cl. ................................ 424/299; 260/345.3; 260/464; 260/465 F; 260/165 R; 260/514 D; 260/557 B; 260/559 R; 260/586 F; 260/598; 260/549; 260/617 R; 424/317; 424/320; 424/324; 560/121; 560/256; 542/426

[58] Field of Search ...................... 260/514 D, 468 D; 424/299, 317

[56] References Cited

U.S. PATENT DOCUMENTS

| | | | |
|---|---|---|---|
| 3,933,842 | 1/1976 | Chadha et al. | 260/468 |
| 3,959,263 | 5/1976 | Abraham et al. | 260/240 |

OTHER PUBLICATIONS

Leeney et al., Prostaglandins, II, 953, (1976).
Corey et al., Tet. Letters, 737, 1976.

*Primary Examiner*—Robert Gerstl
*Attorney, Agent, or Firm*—Stevens, Davis, Miller & Mosher

[57] ABSTRACT

Novel bicycloheptene compounds of the formula:

B, A—Z, X—C, R1, R2, OH wherein A is $C_2$–$C_4$ alkylene; X and B are each ethylene or vinylene; $R_1$ is hydrogen, $C_1$–$C_8$ alkyl, $C_4$–$C_8$ alkoxyalkyl, $C_5$–$C_7$ cycloalkyl, $C_5$–$C_8$ cycloalkylalkyl, aryl, $C_7$–$C_{10}$ arylalkyl, $C_7$–$C_{10}$ aryloxyalkyl; $R_2$ is hydrogen, or $C_1$–$C_4$ alkyl; and Z is carboxyl, $C_2$–$C_5$ alkoxycarbonyl or $C_1$–$C_5$ carbamoyl, and its non-toxic salts, which are useful as antiulcers, gastric secretion inhibitors, central nervous system regulators, and labor inducing agents.

7 Claims, No Drawings

NOVEL BICYCLOHEPTENE DERIVATIVES

The present invention relates to novel bicycloheptene compounds and to their production and use.

More particularly, this invention relates to novel bicycloheptene compounds, to a pharmaceutical composition containing at least one of the bicycloheptene compounds and to a process for their preparation. The novel bicycloheptene compounds of this invention are representable by the following formula;

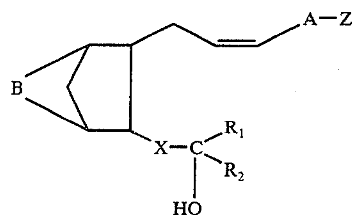

wherein A is $C_2$–$C_4$ alkylene; B and X are each ethylene or vinylene; $R_1$ is hydrogen, $C_1$–$C_8$ alkyl, $C_4$–$C_8$ alkyloxyalkyl, $C_5$–$C_7$ cycloalkyl, $C_5$–$C_8$ cycloalkylalkyl, aryl, $C_7$–$C_{10}$ arylalkyl (aralkyl) or $C_7$–$C_{10}$ aryloxyalkyl; $R_2$ is hydrogen, or $C_1$–$C_4$ alkyl; and Z is carboxyl $C_2$–$C_5$ alkoxycarbonyl or $C_1$–$C_5$ carbamoyl, and its nontoxic salt when Z is carboxyl.

In the significances as used above, "$C_2$–$C_4$ alkylene" means an alkylene having 2 to 4 carbon atoms, of which preferred examples are ethylene, propylene and butylene. "$C_1$–$C_8$ alkyl" means a straight or branched alkyl group having from one to eight carbon atoms (e.g., methyl, pentyl, α-methyl-n-pentyl, α,α-dimethyl-n-pentyl).

Preferred examples of the $C_4$–$C_8$ alkyloxyalkyl are ethoxyethyl, ethoxypropyl, pentoxymethyl, pentoxyethyl, hexoxyethyl, hexoxymethyl, etc.

Preferred examples of the $C_5$–$C_7$ cycloalkyl or $C_5$–$C_8$ cycloalkyalkyl are cyclopentyl, cyclohexyl, cyclopentylmethyl, cyclohexylmethyl and cyclohexylethyl.

Preferred examples of the ary are phenyl and phenyl substituted with $C_1$–$C_4$ alkyl, $C_1$–$C_4$ alkoxy or halogen, and that of the $C_7$–$C_{10}$ arylalkyl are benzyl, phenethyl and phenylpropyl.

Preferred examples of the $C_7$–$C_{10}$ aryloxyalkyl include an alkyl bearing phenoxy or phenoxy substituted with halogen (e.g., chlorine, bromine), $C_1$–$C_4$ alkyl, or $C_1$–$C_4$ alkoxy.

Preferred examples of the $C_2$–$C_5$ alkoxycarbonyl are methoxycarbonyl, and ethoxycarbonyl, and $C_1$–$C_5$ carbamoyl preferably includes carbamoyl, monoalkylcarbamoyl (e.g., N-methylcarbamoyl, N-ethylcarbamoyl), and N,N-dialkylcarbamoyl (e.g. N-dimethylcarbamoyl, N-diethylcarbamoyl). The bicycloheptene compounds (I) of this invention have various useful pharmacological activities and are useful as antiulcer agents, gastric secretion inhibitors, central nervous system regulators, and labor inducing agents.

The bicycloheptene compound (I) has been found to posses anti-gastrointestinal ulcer activity. That is, they inhibit an excessive secretion of gastric acid, and thereby inhibit formation of a gastro intestinal ulcer or heal the ulcer in mammals.

The compounds (I) also show a significant antireserpine or anti-tetrabenazine activity and therefore may be used as psychotropic drugs especially anti-depressant agents. The compounds [I] have been found to possess a smooth-muscle stimulating activity, and therefore may be used as labor inducing agents.

Among the bicycloheptene compounds [I] of this invention, the compounds of the following formula [Ia] are preferable:

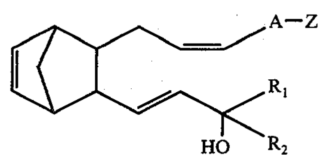

wherein $R_1$, $R_2$, A and Z are as defined above, for instance, in view of their excellent properties as gastric secretion inhibitors and central nervous system regulators. Particularly preferred are the compounds of the following formula [Ib];

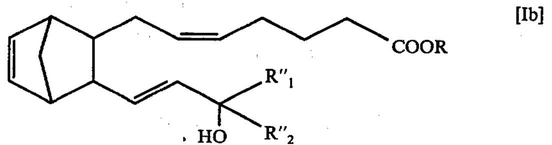

wherein R is hydrogen, methyl or ethyl, $R''_1$ is $C_5$–$C_7$ alkyl, $C_4$–$C_8$ alkyloxyalkyl, $C_5$–$C_7$ cycloalkyl, $C_5$–$C_8$ cycloalkylalkyl, $C_7$–$C_{10}$ arylalkyl or $C_7$–$C_{10}$ aryloxyalkyl and $R''_2$ is hydrogen or methyl.

The novel bicycloheptene compounds [I] of the invention can be prepared by the following methods: Method (a):

The novel bicycloheptene compounds [Ic] of the formula,

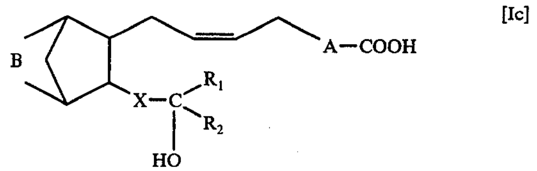

wherein A, B, X, $R_1$ and $R_2$ are as defined above, can be prepared by reacting the compound of the formula [II];

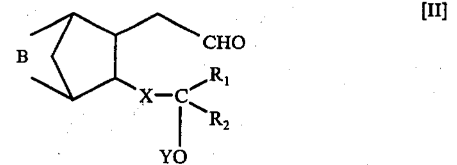

wherein B, X, $R_1$ and $R_2$ are as defined above and Y is hydrogen or a hydroxy protecting group, with a compound of the formula [III];

$$(R')_3P = CH - A - COOM \qquad [III]$$

wherein A is as defined above, R' is an aryl and M is an alkali metal and, if Y is a hydroxy-protecting group, such as tetrahydropyranyl, or alkoxyalkyl, hydrolyzing the resulted products. The Wittig reaction can be carried out in the presence of solvent using 1 - 10 equivalent (preferably 2–4 equivalent) of the Wittig reagent [III]. Examples of the solvent are ethers (e.g. diethylether, tetrahydrofuran, dioxane, dimethoxyethane), hydrocarbons (e.g., benzene, toluene, hexane) and dimethyl sulfoxide. The reaction can be effected ordinally at room temperature, but it can be controlled with warming or cooling depending upon the extent of the progress. The reaction time may vary depending upon the reaction temperature and the reagent to be used therein but generally 2 - 30 hrs. The Wittig reagent [III] can be prepared by reacting a compound of the formula [III-a]:

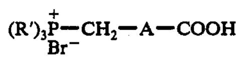

[III-a]

with a base according to known method [E. J. Carey, J. Amer. Chem. Soc., 91 5675 (1969)]. The bicycloheptene compound thus obtained can be separated from the reaction mixture and the bicycloheptene compounds thus obtained, if Y is a hydroxy-protecting group, can be hydrolyzed and purified by the conventional procedures. Method (b):

The novel bicycloheptene compound [*Id*] of the formula;

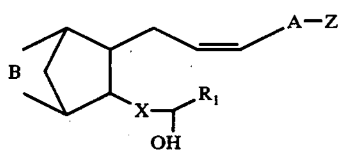

[Id]

wherein A, B, X, $R_1$ and Z are as defined above, can be prepared by reducing a carbonyl compound of the formula [IV]

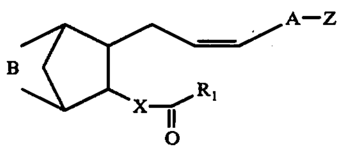

[IV]

wherein A, B, X, Z and $R_1$ are as defined above, with a reducing agent. For this reduction, and of the known reducing agents which can reduce only ketonic carbonyl group without affecting ester or acid groups or carboncarbon double bonds can be used. Examples of such reducing agents are the metal borohydrides, especially sodium, potassium, and zinc borohydrides, lithium (tri-tert-butoxy)aluminum hydride, metal trialkoxy borohydrides, e.g., sodium trimethoxyborohydride, aluminum alkoxide, e.g., aluminum isopropoxide, aluminum ethoxide. The reaction can be carried out in the presence of inert solvent (e.g. alcohol, dioxane, tetrahydrofuran, dimethoxyethane). The reaction condition may vary depending upon the reaction temperature and the reducing agent to be used therein.

The reaction temperature may be from −20° to 20° C. The bicycloheptene compound thus obtained can be separated from the reaction mixture and purified by the conventional procedures.

Method (c):

The novel bicycloheptene compound [Ie] of the formula;

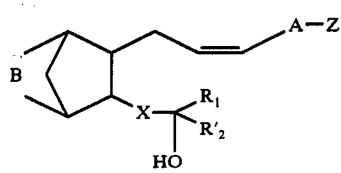

[Ie]

wherein A, B, X, Z and $R_1$ are as defined above and $R'_2$ is a $C_1$–$C_4$ alkyl group, can be prepared by reacting a compound of the formula [IV];

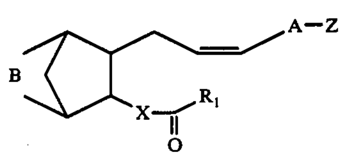

[IV]

wherein A, B, X, Z and $R_1$ are as defined above, with a compound of the formula [V];

$R'_2 — M'$ [V]

wherein $R'_2$ is as defined above, and M' is magnesium halide or alkali metal, or reacting a compound of the formula [VI];

[VI]

wherein A, B, Z, X and $R_2$ are as defined above, with a compound of the formula [VII];

$R'_1 — M'$ [VII]

wherein M' is as defined above, $R'_1$ is as same as $R_1$ excluding hydrogen. The reaction can be carried out in the presence of inert solvent by using the 1 - 1.5 equivalent organic metal compound.

Examples of the inert solvent are ethers (e.g., diethylether, tetrahydrofuran, dimethoxyethane) and hydrocarbons (e.g., benzene, toluene), The organic metal compound can be prepared by the conventional procedures. The reaction conditions may vary depending upon the reaction temperature and the organic metal compound to be used therein, but the temperature is preferably about 0° - 10° C to avoid side reaction. The novel bicycloheptene compound thus obtained can be separated and purified by the conventional procedures.

Among the bicycloheptene compounds [I] thus obtained, the carboxylic acid compound (Z = COOH) can be transformed to its pharmacologically acceptable salt form.

The pharmacologically acceptable salts of these bicycloheptene compounds are those with pharmaceutically acceptable metal cations such as, sodium, potassium, magnesium and calcium, ammonium or amine cations. The novel bicycloheptene compounds of this invention may be administered effectively orally, sublingually, or by intravenous, intramuscular, or subcutaneous injection at a daily dosage of about 1 to 100 mg/kg as gastric secretion inhibitors and antiulcers, and about 1 to 10 mg/kg as anti-depressants.

Starting materials of this invention are prepared by the reactions and procedures described and exemplified hereinafter. The bicycloheptene compounds of the formula [IV] are prepared by the sequence of transformations shown in Charts A and B and the bicycloheptene compounds of the formula [II] are prepared by the sequence of transformations shown in Chart C.

Chart A

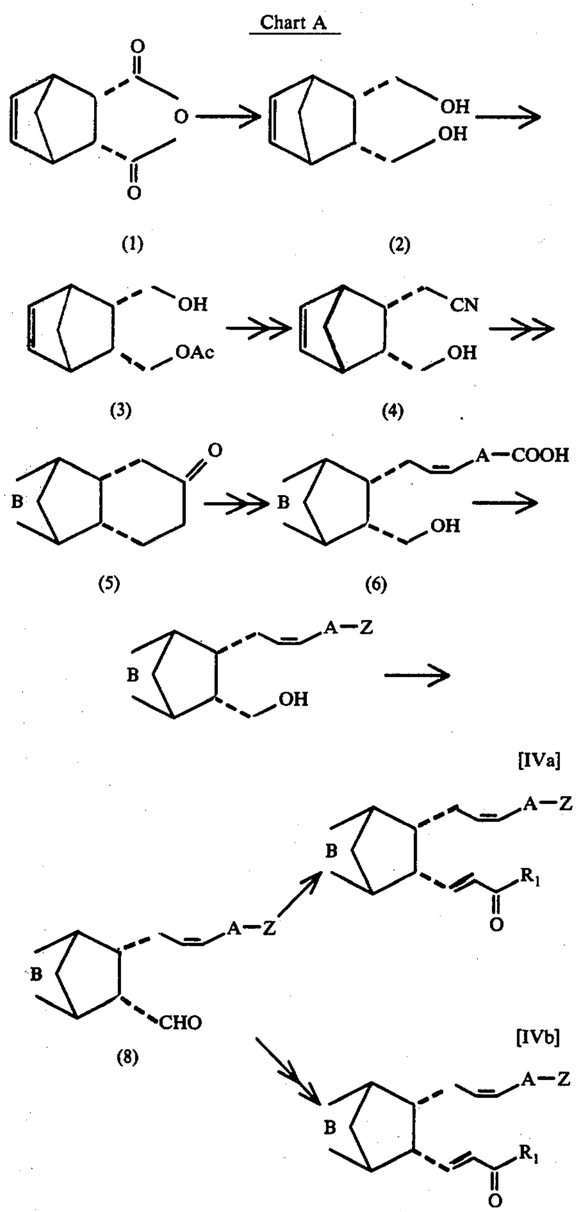

Wherein A, B, Z and $R_1$ are as defined above and Ac is an acyl group or N-alkylcarbamoyl group.

Chart B

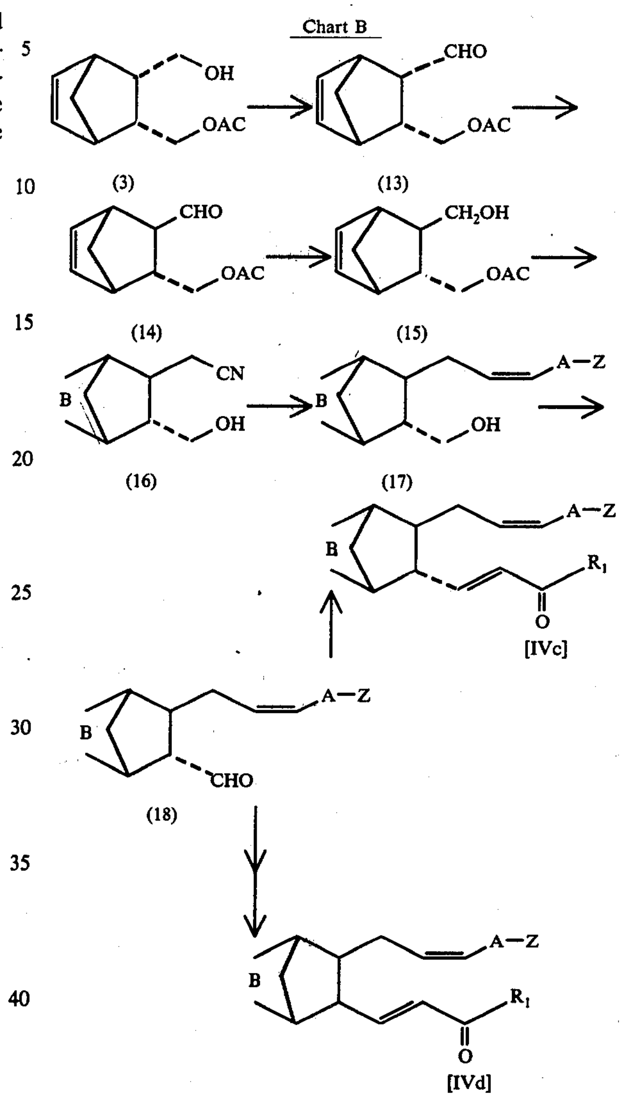

wherein A, B, $R_1$, Z and Ac are as defined above.

Chart C

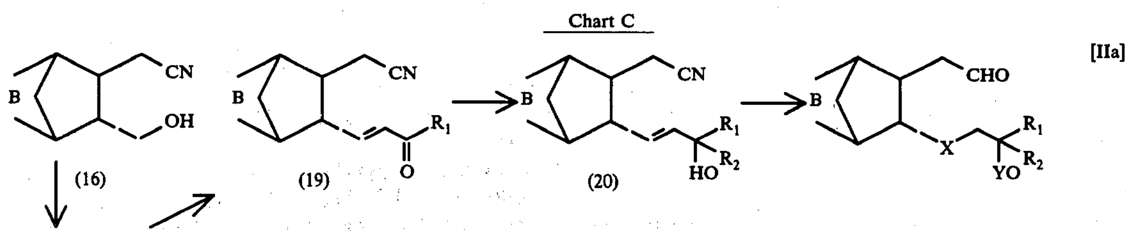

-continued

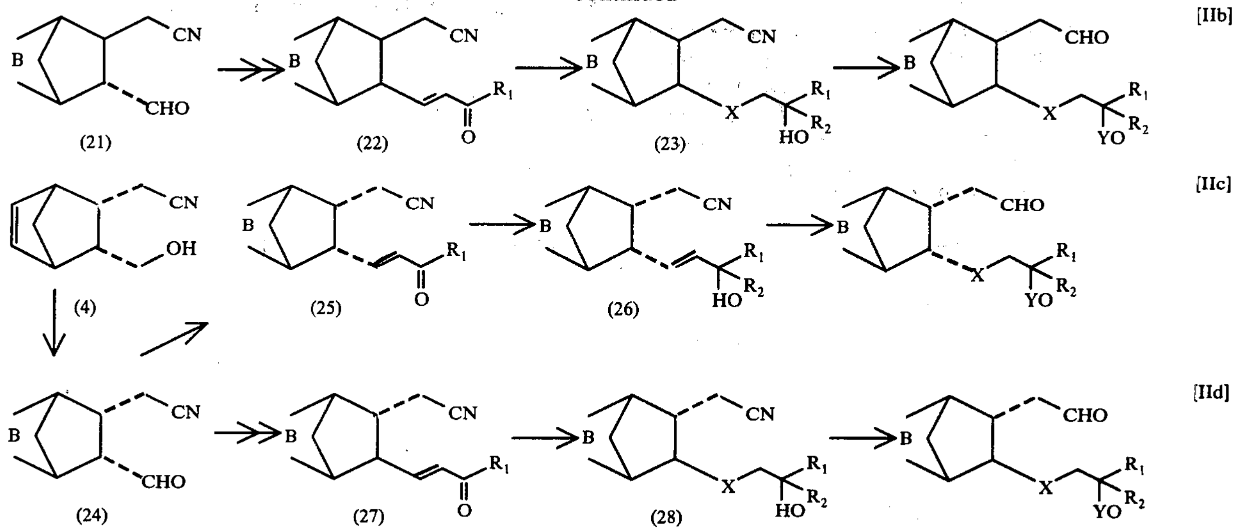

Wherein B, $R_1$, $R_2$, X and Y are as defined above. The compound (4) is obtained from the compound (1) by a sequence of reduction, mono-acylation, tosylation, cyanation and hydrolysis. The transformations of the formula (4) compound to the formula (5) is conducted by hydrolysis, lactonization, and if necessary, reduction. The compound (5) is reduced to give hemiacetal and treated with a Wittig reagent to give a carboxylic acid compound (6). The compound (6) is further esterified or treated with amine to give a compound (7), and the compound (7) is oxidized with Collin's reagent and treated with a Wittig reagent to give the compound [IVa]. On the other hand, the aldehyde compound (8) is epimerized with a catalytic amount of acetic acid and piperidine and followed by treatment with a Wittig reagent to give the compound [IVb]. The transformations of the compound (3) to the compound [IVc] and [IVd] are shown in Chart B.

The transformations of the compound (3) to the compound (16) are conducted by a sequence of oxidation, epimerization, reduction, tosylation, cyanation and if necessary, reduction. The transformations of the compound (16) to the compound [IVc] and [IVd] are accomplished by substantially the same procedures as of Chart A. The preparations of the formylmethylene compound [IIa - d] are shown in Chart C.

The transformations of the compound (16) and (4) to the compound (19), (22), (25) and (27) are also accomplished by substantially the same procedures as described above. The enone compounds (19, etc.) are reduced with a reducing agent such as, zinc borohydride or sodium borohydride, or treated with an organo metal compound such as methyl magnesium iodide to give corresponding hydroxy compounds (20 etc.). The hydroxy compounds (20 etc.) are subjected to reducing with a reducing agent such as diisobutylaluminum hydride with or without protecting a hydroxy group with a hydroxyprotecting group such as dihydropyran to give the formyl methylene compounds [IIa - IId]. The bicycloheptene compounds of this invention have three centers of asymmetry, they can be however encompassed by all stereo-isomers.

The following examples are given for the purpose of illustration and it is not intended to limit the invention.

Experiment

The IR. spectram were taken with a spectrometer Hitachi 285 (Hitachi Co.). The NMR spectra were recorded on a Varian A-60 spectrophotomer with TMS as internal standard.

EXAMPLE 1

To a solution of dry tetrahydrofuran (10 ml), pyridine (5 ml) and 2,3-endo-bishydroxymethyl-bicyclo-[2,2,1]hept-5-ene (3.08 g), was added pivaloyl chloride (2.4 g) at 0° - 5° C. The reaction solution was stirred at room temperature over night and poured into benzene (100 ml). The benzene layer was washed with 10 % aqueous hydrochloric acid (30 ml) and water and dried over $MgSO_4$. Evaporation of the solvent gives an oily crude substance (4.2 g), which was chromatographed on alumina.

An oily 2-endo-hydroxymethyl-3-endo-pivaloyloxymethyl-bicyclo[2,2,1]hept-5-ene (3.4 g) was eluted with benzene-ethyl acetate (10 : 1 ).

IR $\nu_{max}^{film}$ cm$^{-1}$): 3600-3200, 2975, 2925, 2875, 1730, 1480, 1280, 1160

EXAMPLE 2

Into a solution of dry benzene (10 ml), pyridine (10 ml) and 2-endo-hydroxymethyl-3-endopivaloyloxymethyl-bicyclo[2,2,1]hept-5-ene (example 1, 3.4 g), was added p-toluensulfonyl chloride (2.8 g) at 0° - 5° C and the reaction solution was stirred at room temperature overnight and at 70° C for a further 1 hr. The reaction solution was discharged into a mixture of benzene (100 ml) and 10 % HCl (30 ml) and the organic layer was separated, washed, dried and concentrated under reduced pressure to afford the oily objective tosylate derivative (5.7 ). The oily tosylate derivative obtained above was reacted with NaCN in DMSO at 95° - 110° C for 1 hr. to give the oily objective 2-endocyanomethyl-3-endo-pivaloyloxymethyl-bicyclo[2,2,1]hept-5-ene (3.0 g.).

Ir $\nu_{max}^{film}$; 2975, 2925, 2875, 2250, 1730, 1480, 1280, 1160

The cyanomethyl derivative (3.0 g) obtained above was added into 20 % NaOH (13 ml) and refluxed for 7 hr. and conc. HCl was added into the reaction mixture to acidify and the acidic reaction mixture was stirred at room temperature for 1 hr. An objective oily substance was extracted with benzene and the benzene layer was washed, dried and concentrated under reduced pressure to afford oily 2-endo-hydroxymethyl-bicyclo[2,2,1]-hept-5-ene-3-endo-acetic acid lactone (2.0 g).

IR$\nu_{max}^{film}$; 2975, 2925, 2875, 1740, 1480, 1430, 1390, 1350, 1320, 1260, 1160, 1150, 1100, 1040

EXAMPLE 3

To a mixture of dry dichloromethane (150 ml) and Collins' reagent [J. C. Collins et al., Tetrahedron Lett, 3363 (1968)](28 g) at about 10° C under nitrogen was added, with vigorous stirring, a cold (0° - 10° C) solution of 2-endo-hydroxymethyl-3-endo-pivaloyloxymethyl-bicyclo[2,2,1]hept-5-ene (example 1, 3.0 g) in dry dichloromethane (100 ml). After 10 min. additional stirring, dry benzene (100 ml) was added, the mixture was filtered, and the solution was concentrated under reduced pressure to afford the oily 2-endo-formyl derivative. The endo-formyl derivative obtained above was dissolved in benzene (200 ml), and piperidine (10 drops) and acetic acid (10 drops) were added into the solution, and the solution was refluxed for 2.5 hr. under nitrogen, After cooling, the solution was washed with 5 % HCl, aqueous $NaHCO_3$ and water, dried over $MgSO_4$ and concentrated under reduced pressure to afford oily 2-exo-formyl-3-endo-pivaloyloxymethyl-bicyclo[2,2,1]-hept-5-ene (2.5 g).

NMR ($CCl_4$); 9.7 (formyl proton) The exo-formyl derivative obtained above was reduced with sodium borohydride in absolute ethanol at 0° - 10° C to give the oily 2-exo-hydroxymethyl-3-endo-pivaloyloxymethyl-bicyclo[2,2,1]hept-5-ene.

Following the procedure of example 2, there was obtained oily 2-endo-hydroxymethyl-3-exo-cyanomethyl-bicyclo[2,2,1]hept-5-ene (1.1 g).

IR$\nu_{max}^{film}$; 3400, 2225, 1430, 1350, 1260, 1180

EXAMPLE 4

Diisobutylaluminum hyride (3.0 g) in toluene was added dropwise to a stirred solution of 2-endohydroxymethyl-bicyclo[2,2,1]hept-5-ene-3-endo-acetic acid lactone (example 2, 2.9 g) in toluene (30 ml) cooled to −70° C. Stirring was continued for 1 hr. at −70° C, whereupon a solution of aqueous ammonium chloride was cautiously added. The mixture was filtered and the filtrate was washed with brine, dried, and concentrated to afford an oily hemiacetal. 4-Carboxybutyl triphenylphosphonium bromide (15.58 g) was added to a solution of sodio dimethylsulfinylcarbanide prepared from sodium hydride (65 %, 2.6 g) and dimethyl sulfoxide (DMSO) and the mixture was stirred for 10 min. at about 20° C. To this reagent was added dropwise the hemiacetal obtained above in DMSO (5 ml). The mixture was stirred at room temperature over night, then diluted with benzene (50 ml) and poured into water. The aqueous layer was separated and acidified with conc. hydrochloric acid, then the objective carboxylic acid was extracted with ethyl acetate. The organic layer was washed with brine, dried and concentrated to afford a crude carboxylic acid derivative, which was esterified with methanol and conc. sulfuric acid (trace) to give the crude objective carboxylate. Purification with silicagel chromatography gave the oily objective 2-endo-hydroxymethyl-3-endo-(6'-carbomethoxy-2'-cis-hexenyl)-bicyclo[2,2,1]hept-5-ene (3.8 g).

IR$\nu_{max}^{film}$; 3600-3200, 2950, 2850, 1740, 1440, 1240, 1160

EXAMPLE 5

Following the procedures of example 4, 2-endo-hydroxymethyl-3-exo-cyanomethyl-bicyclo[2,2,1]-hept-5-ene (example 3, 1 g) was reduced with diisobutylaluminium hydride, treated with Wittig reagent (4-carboxybutyl triphenylphosphonium bromide) and esterified to give the oily objective 2-endo-hydroxymethyl-3-exo-(6'-carbomethoxy-2'-cis-hexenyl)-bicyclo-[2,2,1]hept-5-ene (600 mg).

IR$\nu_{max}^{film}$; 3600-3200, 2950, 1740, 1440, 1240, 1160

EXAMPLE 6

Following the procedures of example 3, 2-endo-hyroxymethyl-3-endo-(6'-carbomethoxy-2'-cishexenyl)-bicyclo[2,2,1]hept-5-ene (example 4, 500 mg) was oxidized with Collins' reagent to give oily 2-endo-formyl-3-endo-(6'-carbomethoxy-2'-cis-hexenyl)bicyclo[2,2,1]-hept-5-ene. A solution of dimethyl hexanoylmethyl phosphonate (500 mg) in dry THF was added, with stirring, to a cold (5° C) suspension of sodium hydride (65 % 83 mg) in THF (10 ml). Thereafter the reaction mixture was stirred at room temperature for 1.5 hr, and cooled to 5° C. To the mixture was added a THF solution of endo-formyl derivative obtained above. After 2hr, acetic acid was added and the solvent distilled off under reduced pressure. The residue was dissolved in benzene and the solution was washed with brine, dried and concentrated under reduced pressure. Chromatography on silicagel using benzene for elution yielded the oily objective 2-endo-(3'-oxo-1'-trans-octenyl)-3-endo(6'-carbomethoxy-2'-cis-hexenyl)-bicyclo[2,2,1]-hept-5-ene (580 mg).

IR$\nu_{max}^{film}$; 3050, 2950, 2875, 1740, 1695, 1670, 1620, 1440, 1360, 1240, 1200, 1170

Following the same procedures, using 2-endo-hydroxymethyl-3-exo-(6'-carbomethoxy-2'-cis-hexenyl)-bicyclo[2,2,1]hept-5-ene, (example 5) there was obtained oily 2-endo-(3'-oxo-1'-trans-octenyl)-3-exo(6'-carbomethoxy-2'-cis-hexenyl)-bicyclo[2,2,1]hept-5-ene.

IR$\mu_{max}^{film}$; 3050, 2950, 2875, 1740, 1695, 1670, 1620, 1460, 1440, 1360, 1240, 1160

Following the same procedures, but replacing the Wittig reagent (dimethyl hexanoylmethylphosphonate) with another Wittig reagents (J. Am. Chem. Soc., 91 5675 (1969) and, Chem. Rev., 74 87), there were obtained the following compounds, 2-endo-(3'-oxo-4'-methyl-1'-trans-octenyl)-3-exo-(6'-carbomethoxy-2'-cis-hexenyl)-bicyclo[2,2,1]-hept-5-ene, oily substance.

IR$\nu_{max}^{film}$; 3050, 2950, 2925, 2875, 1740, 1690, 1670, 1620, 1450, 1420, 1380

2-endo-(3'-oxo-1'-trans-butenyl)-3-exo(6'-carbomethoxy-2'-cis-hexenyl)-bicyclo[2,2,1]hept-5-ene, oily substance.

IR$\nu_{max}^{film}$; 3050, 2950, 2850, 1740, 1690, 1670, 1620, 1440, 1370

EXAMPLE 7

Following the procedures of examples 3 and 6, 2-endo-formyl-3-endo-(6'-carbomethoxy-2'-cis-hexenyl)-bicyclo[2,2,1]hept-5-ene (example 6, 2.6 g) was subjected to epimerization and treated with the Wittig reagent (dimethyl hexanoylmethylphosphonate) to give oily 2-exo-(3'-oxo-1'-trans-octenyl)-3-endo-(6'-carbomethoxy-2'-cis-hexenyl)-bicyclo[2,2,1]hept-5-ene (2.8 g).

IR$\nu_{max}^{film}$; 3050, 2950, 2875, 1740, 1700, 1670, 1620, 1440, 1360, 1240, 1200, 1170

Following the same procedures, there were obtained the following compounds.

2-exo-(3'-oxo-1'-trans-octenyl)-3-exo-(6'-carbomethoxy-2'-cis-hexenyl)-bicyclo[2,2,1]hept-5-ene, oily substance.

IR$\nu_{max}^{film}$; 3050, 2950, 2875, 1740, 1695, 1670, 1620, 1460, 1360, 1240, 1170

2-exo-(3'-oxo-4'-methyl-1'-trans-octenyl)-3-endo-(6'-carbomethoxy-2'-cis-hexenyl)-bicyclo[2,2,1]hept-5-ene, oily substance IR$\nu_{max}^{film}$; 3050, 2950, 2925, 2875, 1740, 1690, 1660, 1620, 1460, 1420, 1380

2-exo-(3'-oxo-4',4'-dimethyl-1'-trans-octenyl)-3-endo-(6'-carbomethoxy-2'-cis-hexenyl)-bicyclo[2,2,1]-hept-5-ene, oily substance.

IR$\nu_{max}^{film}$; 3050, 2950, 2925, 2875, 1740, 1690, 1620, 1460, 1360

2-exo-(3'-oxo-7'-methyl-1'-trans-octenyl)-3-endo-(6'-carbomethoxy-2'-cis-hexenyl)-bicyclo[2,2,1]hept-5-ene, oily substance.

IR$\nu_{max}^{film}$; 3050, 2950, 2850, 1740, 1690, 1670, 1620, 1440, 1370

2-endo-(3'-oxo-1'-trans-butenyl)-3-exo-(6'-carbomethoxy2'-cis-hexenyl)-bicyclo[2,2,1]hept-5-ene, oily substance.

IR$\nu_{max}^{film}$; 3050, 2950, 2850, 1740, 1690, 1670, 1620, 1440, 1370

2-exo-(3'-oxo-4'-cyclohexyl-1'-trans-butenyl)-3-endo-(6'-carbomethoxy-2'-cis-hexenyl)-bicyclo[2,2,1]hept-5-ene, oily substance.

IR$\nu_{max}^{film}$; 3050, 2950, 2850, 1740, 1690, 1660, 1620, 1450, 1380, 1240

2-exo-(3'-oxo-4'-phenyl-1'-trans-butenyl)-3-endo-(6'-carbomethoxy-2'-cis-hexenyl)-bicyclo[2,2,1]hept-5-ene, oily substance.

IR$\nu_{max}^{film}$; 3050, 2950, 2850, 1740, 1690, 1670, 1620, 1440, 1370

2-exo-(3'-oxo-1'-trans-propenyl)-3-endo-(6'-carbomethoxy2'-cis-hexenyl)-bicyclo[2,2,1]hept-5-ene, oily substance.

IR$\nu_{max}^{film}$; 3050, 2950, 2925, 1740, 1690, 1470, 1370, 1340, 1280

2-exo-(3'-oxo-1'-trans-4'-amyloxy-butenyl)-3-endo-(6'-carbomethoxy-2'-cis-hexenyl)-bicyclo[2,2,1]hept-5-ene, oily substance.

IR$\nu_{max}^{film}$; 3050, 2950, 2850, 1740, 1690, 1620, 1440, 1360

2-exo-(3'-oxo-5'-ethoxy-1'-trans-pentenyl)-3-endo-(6'-carbomethoxy-2'-cis-hexenyl)-bicyclo[2,2,1]hept-5-ene, oily substance.

IR$\nu_{max}^{film}$; 3050, 2975, 2875, 1740, 1700, 1670, 1620, 1440, 1380, 1360, 1250, 1180

2-exo-(3'-oxo-1'-trans-4'-phenoxy-butenyl)-3-endo-(6'-carbomethoxy-2'-cis-hexenyl)-bicyclo[2,2,1]hept-5-ene, oily substance.

IR$\nu_{max}^{film}$; 2950, 2875, 1740, 1690, 1620, 1600, 1500, 1440, 1370, 1220, 1170

2-exo-(3'-oxo-1'-trans-4'-p-fluorophenoxy-butenyl)-3-endo-(6'-carbomethoxy-2'-cis-hexenyl)-bicyclo[2,2,1]-hept-5-ene, oily substance.

IR$\nu_{max}^{film}$; 2950, 2850, 1740, 1695, 1620, 1600, 1500, 1440, 1220, 1110

EXAMPLE 8

A solution of methanol (25 ml), 10 % aqueous sodium hydroxide (20 ml) and 2-endo-cyanomethyl-3-endo-pivaloyloxymethyl-bicyclo[2,2,1]hept-5-ene (example 2, 1.1 g) was stirred at room temperature for 5 hr. and concentrated under reduced pressure. The residue was extracted with benzene and the benzene layer was washed, dried and concentrated to give oily 2-endo-cyanomethyl-3-endo-hydroxymethyl-bicyclo[2,2,1]-hept-5-ene (700 mg).

IR$\nu_{max}^{film}$; 3650-3150, 3050, 2950, 2250, 1420, 1340

Following the procedures of example 3, using the endohydroxymethyl derivative (4.5 g) obtained above, there was obtained oily 2-exo-formyl-3-endo-cyanomethylbicyclo[2,2,1]hept-5-ene.

NMR ($CCl_4$) 9.75 ppm (formyl proton)

Following the procedures of example 7, using 2-exo-formyl derivative obtained above with Wittig reagent (dimethyl hexanoylmethyl phosponate), there was obtained oily 2-exo-(3'-oxo-1'-trans-octenyl)-3-endo-cyanomethyl-bicyclo[2,2,1]hept-5-ene (4.2 g)

IR$\nu_{max}^{film}$; 2950, 2925, 2875, 2250, 1695, 1670, 1620, 1480, 1460, 1420, 1370, 1340

Following the same procedures, there was obtained the following compounds.

2-exo-(3'-oxo-1'-trans-4'-methyl-octenyl)-3-endocyanomethyl-bicyclo[2,2,1]hept-5-ene, oily substance IR$\nu_{max}^{film}$; 3050, 2950, 2875, 2250, 1690, 1660, 1620, 1460, 1420, 1380, 1340, 1220, 1180

2-endo-(3'-oxo-1'-trans-octenyl)-3-exo-cyanomethyl-bicyclo[2,2,1]hept-5-ene, oily substance.

IR$\nu_{max}^{film}$; 3050, 2950, 2875, 2250, 1700, 1670, 1630, 1480, 1460, 1420, 1340

2-endo-(3'-oxo-1'-trans-4'-methyl-octenyl)-3-exocyanomethyl-bicyclo[2,2,1]hept-5-ene, oily substance.

IR$\nu_{max}^{film}$; 3050, 2950, 2925, 2875, 2250, 1710, 1660, 1620, 1460, 1420, 1380, 1340, 1220

2-(4'-phenyl-3'-oxo-1'-trans-butenyl)-3-cyanomethyl-bicyclo[2,2,1]hept-5-ene, oily substance.

IR$\nu_{max}^{film}$; 3060, 2960, 2930, 2850, 2250, 1690, 1670, 1620, 1460, 1370

EXAMPLE 9

2-endo-hydroxymethyl-3-exo-cyanomethylbicyclo[2,2,1]hept-5-ene (example 3, 700 mg) was hydrogenated with 5 % Pd-C in methanol under atmospheric pressure. The methanolic solution thus obtained was filtered to remove the catalyst, and the filtrate was concentrated to afford oily 2-endo-hydroxymethyl-3-exo-cyanomethyl-bicyclo[2,2,1]heptane (700 mg).

IR$\nu_{max}^{film}$; 3600-3100, 2925, 2225, 1450, 1420

Following the procedures of example 8, using the endohydroxymethyl derivative obtained above, there was obtained oily 2-endo-(3'-oxo-1'-trans-4'-ethyloctenyl)-3-exo-cyanomethyl-bicyclo[2,2,1]heptane (710 mg)

IR$\nu_{max}^{film}$; 2950, 2875, 2250, 1690, 1660, 1620, 1460, 1420, 1380

EXAMPLE 10

A solution containing 2-exo-(3'-oxo-1'-transoctenyl)-3-endo-(6'-carbomethoxy-2'-cis-hexenyl)bicyclo[2,2,1]-hept-5-ene (example 7, 500 mg) was added to a mixture of zinc borohydride prepared from zinc chloride (anhydrous, 680 mg) and sodium borohydride (380 mg) in dimethoxyethane, with stirring and cooling to −20° C. Stirring was continued for 4 hr at −20° C and at room temperature for a further 1 hr. After consumption of the excess zinc borohydride by addition of acetone, the reaction mixture was concentrated to give a sirupy residue, which was decomposed with an aq. solution of ammonium chloride. The resulting oily layer was extracted with benzene. The extract was washed with brine, dried and concentrated to given an oily substance, which was chromatographed on silicagel. Elution with benzene gave oily 2-exo-(3'-hydroxy-1'-trans-octenyl)-3-endo-(6'-carbomethoxy-2'-cis-hexenyl)-bicyclo[2,2,1]hept-5-ene (450 mg).

IR$\nu_{max}^{film}$; 3600-3100, 3050, 2950, 2925, 2850, 1740, 1450, 1430, 1360

Following the same procedures, there were obtained the following compounds.

2-endo-(3'-hydroxy-1'-trans-octenyl)-3-exo-(6'-carbomethoxy-2'-cis-hexenyl)-bicyclo[2,2,1]hept-5-ene, oily substance IR$\nu_{max}^{film}$; 3600-3100, 3050, 2950, 2925, 2850, 1740, 1450, 1430, 1360

2-exo-(3'-hydroxy-4'-methyl-1'-trans-octenyl)-3-endo-(6'-carbomethoxy-2'-cis-hexenyl)-bicyclo[2,2,1]hept5-ene, oily substance.

IR$\nu_{max}^{film}$; 3650-3200, 3050, 2950, 2925, 2850, 1740, 1450, 1430, 1370, 1210

2-endo-(3'-hydroxy-4'-methyl-1'-trans-octenyl)-3-exo-(6'-carbomethoxy-2'-cis-hexenyl)-bicyclo[2,2,1]hept-5-ene, oily substance.

IR$\nu_{max}^{film}$; 3600-3100, 3050, 2950, 2925, 2850, 1740, 1450, 1430, 1370, 1210

2-exo-(3'-hydroxy-4',4'-dimethyl-1'-trans-octenyl)--endo-(-endo(6'-carbomethoxy-2'-cis-hexenyl)-bicyclo[2,2,1-hept-5-ene, oily substance.

IR$\nu_{max}^{film}$; 3600-3200, 3050, 2950, 2875, 1740, 1460, 1420, 1360, 1330, 1210, 1160

2-exo-(3'-hydroxy-7'-methyl-1'-trans-octenyl)-3-endo-(6'-carbomethoxy-2'-cis-hexenyl)-bicyclo[2,2,1]hept-5-ene, oily substance IR$\nu_{max}^{film}$; 3600-3200, 3050, 2975, 2950, 2850, 1740, 1450, 1430, 1370, 1210

2-endo-(3'-hydroxy-1'-trans-butenyl)-3-exo-(6'-carbomethoxy-2'-cis-hexenyl)-bicyclo[2,2,1]hept-5-ene, oily substance.

IR$\nu_{max}^{film}$; 3600-3200, 3050, 2950, 2850, 1740, 1450, 1370, 1340, 1240, 1160

2-exo-(3'-hydroxy-4'-cyclohexyl-1'-trans-butenyl)-3-endo-(6'-carbomethoxy-2'-cis-hexenyl)-bicyclo[2,2,1]-hept-5-ene, oily substance.

IR$\nu_{max}^{film}$; 3600-3200, 3050, 2900, 2850, 1740, 1480, 1440, 1330, 1240

2-exo-(3'-hydroxy-1'-trans-propenyl)-3-endo-(6'-carbomethoxy-2'-cis-hexenyl)-bicyclo[2,2,1]hept-5-ene, oily substance.

IR$\nu_{max}^{film}$; 3600-3150, 2950, 2875, 1740, 1470, 1420, 1390, 1180

2-exo-(3'-hydroxy-4'-phenyl-1'-trans-butenyl)-3-endo-(6'-carbomethoxy-2'-cis-hexenyl)-bicyclo[2,2,1]hept-5-ene, oily substance.

IR$\nu_{max}^{film}$; 3600-3200, 3050, 2950, 2875, 1740, 1600, 1500, 1450, 1440, 1360, 1340, 1240

2-exo-(3'-hydroxy-4'-amyloxy-1'-trans-butenyl)-3-endo-(6'-carbomethoxy-2'-cis-hexenyl)-bicyclo[2,2,1]hept-5-ene, oily substance.

IR$\nu_{max}^{film}$; 3600-3200, 2950, 2850, 1740, 1480, 1450, 1440, 1360, 1310, 1210, 1110

2-exo-(3'-hydroxy-5'-ethoxy-1'-trans-pentenyl)-3-endo-(6'-carbomethoxy-2'-cis-hexenyl)-bicyclo[2,2,1]hept-5-ene, oily substance.

IR$\nu_{max}^{film}$; 3600-3200, 3050, 2975, 2875, 1740, 1440, 1380, 1360, 1250, 1110

2-exo-(3'-hydroxy-1'-trans-4'-phenoxy-butenyl)-3-endo-(6'-carbomethoxy-2'-cis-hexenyl)-bicyclo[2,2,1]hept-5-ene IR$\nu_{max}^{film}$; 3600-3200, 2975, 2875, 1740, 1610, 1500, 1440, 1220, 1170

2-exo-(3'-hydroxy-1'-trans-4'-p-fluorophenoxy-butenyl)-3-endo-(6'-carbomethoxy-2'-cis-hexenyl)-bicyclo[2,2,1]-hept-5-ene IR$\nu_{max}^{film}$; 3600-3200, 2975, 2850, 1740, 1600, 1500 1440, 1220, 1110

2-endo-(3'-hydroxy-1'-trans-octenyl)-3-endo-(6'-carbomethoxy-2'-cis-hexenyl)-bicyclo[2,2,1]hept-5-ene as an oily substance IR$\nu_{max}^{film}$; 3600-3200, 3050, 2950, 2925, 2850, 1740, 1440, 1360, 1250, 1160

EXAMPLE 11

Into a solution containing 2-exo-(3'-oxo-1'-trans-octenyl)-3-endo-(6'-carbomethoxy-2'-cis-hexenyl)-bicyclo[2,2,1]hept-5-ene (example 7, 300 mg) in dry THF (15 ml), was added a solution of methylmagnesium iodide (1.1 equivalent) in dry ether at 10° -15° C. Stirring was continued for 2 hr at room temperature. After decomposition of the complex by addition of a solution of aq. ammonium chloride, the reaction mixture was concentrated. The resulting oily layer was extracted with benzene and the benzene layer was washed with brine, dried and concentrated to afford an oily substance, which was chromatographed on silicagel. Elution with benzene gave oily 2-exo-(3'-hydroxy-3'-methyl-1'-transoctenyl)-3-endo-(6'-carbomethoxy-2'-cis-hexenyl)-bicyclo-[2,2,1]hept-5-ene (263 mg).

IR$\nu_{max}^{film}$; 3600-3200, 3050, 2950, 2925, 2850, 1740, 1450, 1430, 1360

EXAMPLE 12

Following the procedures of example 10, reduction of oxo-derivative, there were obtained the following compounds wherein the starting materials were obtained by the method of example 8.

2-exo-(3'-hydroxy-1'-trans-octenyl)-3-endo-cyanomethylbicyclo[2,2,1]hept-5-ene, oily substance.

IR$\nu_{max}^{film}$; 3600-3200, 2950, 2925, 2850, 2255, 1460, 1420, 1340

2-exo-(3'-hydroxy-4'-methyl-1'-trans-ocetenyl)-3-endocyanomethyl-bicyclo [2,2,1]hept-5-ene, oily substance IR$_{max}^{film}$; 3600-3200, 3050, 2950, 2925, 2875, 2250, 1460, 1420, 1380, 1340, 1250

2-endo-(3'-hydroxy-4'-methyl-1'-trans-octenyl)-3-exocyanomethyl-bicyclo[2,2,1]hept-5-ene, oily substance.

IR$\nu_{max}^{film}$; 3600-3200, 3050, 2950, 2875, 2250, 1460, 1420, 1380, 1250

2-endo-(3'-hydroxy-1'-trans-octenyl)-3-exo-cyanomethylbicyclo[2,2,1]hept-5-ene, oily substance IR$\nu_{max}^{film}$; 3600-3200, 3050, 2950, 2925, 2850, 2250, 1460, 1420, 1340

2-endo-(3'-hydroxy-4'-ethyl-1'-trans-oectenyl)-3-exo-cyanomethyl-bicyclo[2,2,1]heptane, oily substance IR$\nu_{max}^{film}$; 3600-3200, 2950, 2875, 1460, 1420, 1400, 1330, 1140

EXAMPLE 13

Following the procedures of example 11, using 2-exo-(3'-oxo-1'-trans-octenyl)-3-endo-cyanomethyl-bicyclo[2,2,1]hept-5-ene (example 8, 2.0 g), there was obtained 2-exo-(3'-hydroxy-3'-methyl-1'-trans-octenyl)-3-endo-cyanomethyl-bicyclo[2,2,1]hept-5-ene (1.6 g) as an oily substance.

IR$\nu_{max}^{film}$; 3600-3200, 3050, 2950, 2925, 2250, 1460, 1420, 1370, 1340, 1150

EXAMPLE 14

A solution of 2-exo-(3'-hydroxy-1'-transoctenyl)-3-endo-cyanomethyl-bicyclo[2,2,1]hept-5-ene (example 12, 1.2 g), dihydropyrane (3 g) and p-toluenesulfonic acid (100 mg) in dichloromethane (10 ml) was stirred at room temperature for 5 hr. The solution was washed with sidium bicarbonate solution, dried and concentrated under reduced pressure to yield the objective 2-exo-(3'-tetrahydropyranyloxy-1'-trans-octenyl)-3-endocyanomethyl-bicyclo[2,2,1]hept-5-ene (1.3 g) as an oily substance. Diisobutylaluminum hydride (9.7 m mol in tuluene) was added dropwise to a stirred solution of the tetrahydropyranyl ethers obtained above in toluene (20 ml) at −60° - −50° C under nitrogen.

Stirring was continued at −70° C for 4 hr, wherein a solution of aq. ammonium chloride (5 ml) was added. After 15 minutes, a solution of 1 % aq. hydrochloric acid (10 ml) was added to the reaction mixture and the solution was stirred for 30 min. at room temperature. The organic layer was separated, washed with brine, dried and concentrated to give 2-exo-(3'-tetrahydropyranyloxy-1'-trans-octenyl)-3-endoformylmethyl-bicyclo[2,2,1]hept-5-ene (1.3 g) as an oily substance.

IR$\nu_{max}^{film}$; 3050, 2975, 2950, 2800, 2700, 1720, 1470, 1460, 1440, 1370, 1350, 1340.

4-Carboxy butyl triphenylphosphonium bromide (6.8 g) was added to a solution of sodio dimethylsulfinylcarbanide prepared from sodium hydride (50 %, 1.476 g) and DMSO (30 ml) and the mixture was stirred for 20 min. at 20° C. To this Wittig reagent was added the formyl methyl derivative obtained above in DMSO (5 ml). The mixture was stirred about 25° C for 18 hr, then diluted with benzene (100 ml). To it was added dropwise water with cooling and stirring. The aqueous layer separated was acidified carefully with 10 % aqueous hydrochloric acid. The oily substance was extracted with ethyl acetate and the ethyl acetate layer was washed with brine, dried and concentrated to give crude oily substance. The crude oily substance was esterified with diazomethane in ether. The crude methyl ester derivative thus obtained was chromatographied on silicagel. Elution with benzene gave 2-exo-(3'-tetrahydropyranyloxy-1'-trans-octenyl)-3-endo-(6'-carbomethoxy-2'-cis-hexenyl)-bicyclo[2,2,1]hept-5-ene (550 mg) as an oily substance.

IR$\nu_{max}^{film}$; 3050, 2950, 2875, 1740, 1470, 1450, 1440, 1370, 1240, 1020.

To a solution of acetic acid, water and THF (20 : 10 : 3), was added the tetrahydropyranyl ether derivative obtained above, and the solution was stirred at 40° C for 6 hr and concentrated under reduced pressure to yield an oily residue, which was extracted with benzene. The benzene layer was washed with aq. $NaHCO_3$ and brine, dried and concentrated under reduced pressure to afford oily 2-exo-(3'-hydroxy-1'-trans-octenyl)-3-endo-(6'-carbomethoxy-2'-cis-hexenyl)-bicyclo[2,2,1]hept-5-ene.

This product was identified with the compound obtained in example 10 in their IR spectrum.

Following the same procedures, there were obtained the following compounds.

2-exo-(3'-hydroxy-3'-methyl-1'-trans-octenyl)-3-endo-(6'-carbomethoxy-2'-cis-hexenyl)-bicyclo[2,2,1]hept-5-ene, oily substance.

This product was identified with the compound obtained in example 11 in their IR spectrum.

2-endo-(3'-hydroxy-1'-trans-octenyl)-3-exo-(6'-carbomethoxy-2'-cis-hexenyl)-bicyclo[2,2,1]hept-5-ene, oily substance.

This product was identified with the compound obtained in example 10 in their IR spectrum.

EXAMPLE 15

A solution of 2-exo-(3'-hydroxyl-1'-transoctenyl)-3-endo-(6'-carbomethoxy-2'-cis-hexenyl)-bicyclo[2,2,1]-hept-5-ene (example 10, 1.0 g) in methanol (20 ml) and 5 % aq. NaOH (10 ml) was stirred at 0° - 5° C for 2 hr and concentrated under reduced pressure to afford a syrupy residue. To this syrupy residue, was added ether and 10 % aq. HCl to acidify (pH 3) and the ether layer was separated, washed with brine, dried and concentrated to yield 2-exo-(3'-hydroxy-1'-trans-octenyl)-3-endo-(6'-carboxy-2'-cis-hexenyl)-bicyclo[2,2,1]hept-5-ene as an oily substance (850 mg).

IR$\nu_{max}^{film}$; 3600-2500, 3050, 2950, 2925, 2850, 1710, 1450, 1400, 1340, 1240.

Following the same procedures, each of the ester derivatives obtained in examples 10, 11 and 14 can be transformed to the corresponding carboxylic acid derivative.

What we claimed is:

1. A compound of the formula

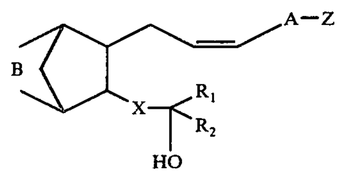

wherein A is $C_2$–$C_4$ alkylene, B and X are each ethylene or vinylene, $R_1$ is hydrogen $C_1$–$C_8$ alkyl, $C_4$–$C_8$ alkyloxyalkyl, $C_5$–$C_7$ cycloalkyl, $C_5$–$C_8$ cycloalkylalkyl, $R_2$ is hydrogen or $C_1$–$C_4$ alkyl and Z is carboxyl or its non-toxic salt, or $C_2$–$C_5$ alkoxycarbonyl carbamoyl.

2. A compound of the formula,

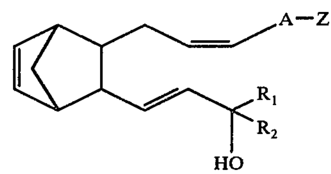

wherein A is $C_2$–$C_4$ alkylene, $R_1$ is $C_1$–$C_8$ alkyl, $C_4$–$C_8$ alkyloxyalkyl, $C_5$–$C_7$ cycloalkyl, $C_5$–$C_8$ cycloalkylalkyl, $R_2$ is hydrogen or $C_1$–$C_4$ alkyl and Z is carboxyl or its non-toxic salt, or $C_2$–$C_5$ alkoxycarbonyl.

3. A compound of the formula,

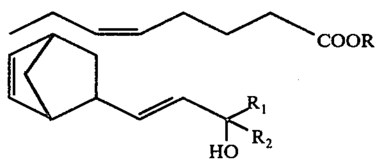

wherein R is hydrogen or $C_1$–$C_2$ alkyl, $R_1$ is $C_5$–$C_7$ alkyl, $C_4$–$C_8$ alkyloxyalkyl, $C_5$–$C_7$ cycloalkyl, or $C_5$–$C_8$ cycloalkylalkyl, and $R_2$ is hydrogen or a $C_1$–$C_4$ alkyl.

4. 2-exo-(3'-Hydroxy-1'-trans-octenyl)-3-endo-(6'-carboxy-2'-cis-hexenyl)-bicyclo[2,2,1]hept-5-ene.

5. 2-exo-(3'-Hydroxy-3'-methyl-1'-trans-octenyl)-3-endo-(6'-carboxy-2'-cis-hexenyl)-bicyclo[2,2,1]hept-5-ene.

6. 2-exo-(3'-Hydroxy-4',4'-dimethyl-1'-trans-octenyl)-3-endo-(6'-carboxy-2'-cis-hexenyl)-bicyclo-[2,2,1]hept-5-ene.

7. A psychotropic, antiulcer and labor-inducing pharmaceutical composition comprising as an active ingredient an effective amount of at least one of the compounds claimed in claim 1 with at least one pharmaceutically inert carrier or diluent.

* * * * *